(12) United States Patent
Bates

(10) Patent No.: US 8,257,384 B2
(45) Date of Patent: Sep. 4, 2012

(54) INTERVENTIONAL CATHETER FOR RETROGRADE USE HAVING EMBOLIC PROTECTION CAPABILITY AND METHODS OF USE

(75) Inventor: Mark C. Bates, Charleston, WV (US)

(73) Assignee: Nexeon MedSystems, Inc., Charleston, WV (US)

( * ) Notice: Subject to any disclaimer, the term of this patent is extended or adjusted under 35 U.S.C. 154(b) by 117 days.

(21) Appl. No.: 12/945,729

(22) Filed: Nov. 12, 2010

(65) Prior Publication Data

US 2011/0098739 A1  Apr. 28, 2011

Related U.S. Application Data

(63) Continuation of application No. 11/315,463, filed on Dec. 21, 2005, now Pat. No. 7,837,702.

(51) Int. Cl.
*A61M 25/00* (2006.01)
(52) U.S. Cl. .................................................. 606/200
(58) Field of Classification Search ................. 600/562; 604/104–106; 606/110, 113, 114, 127, 128, 606/200; 623/1.11
See application file for complete search history.

(56) References Cited

U.S. PATENT DOCUMENTS

| | | | |
|---|---|---|---|
| 4,723,549 A | 2/1988 | Wholey et al. | |
| 5,011,488 A | 4/1991 | Ginsburg | |
| 5,102,415 A | 4/1992 | Guenther et al. | |
| 5,246,445 A | 9/1993 | Yachia et al. | |
| 5,549,626 A | 8/1996 | Miller et al. | |
| 5,910,154 A | 6/1999 | Tsugita et al. | |
| 6,036,717 A | 3/2000 | Mers Kelly et al. | |
| 6,042,598 A | 3/2000 | Tsugita et al. | |
| 6,136,016 A | 10/2000 | Barbut et al. | |
| 6,206,868 B1 | 3/2001 | Parodi | |
| 6,395,014 B1 | 5/2002 | Macoviak et al. | |
| 6,540,768 B1 | 4/2003 | Diaz et al. | |
| 6,592,606 B2 | 7/2003 | Huter et al. | |
| 2002/0095172 A1 | 7/2002 | Mazzocchi et al. | |

OTHER PUBLICATIONS

Roth, First Artificial Muscle Arrays form Carbon Nanotubes, Max Planck Society for the Advancement of Science Research News Release, May 18, 1999, 3 pages, Max Planck Institute for Solid State Research, Germany. http://www.mpg.de/english/illustrationsDocumentation/documentation/pressReleases/1999/news26.sub.--99.htm.
PCT International Search Report for PCT/US06/048921, 2 pages (mailed Oct. 22, 2008).
PCT Written Opinion of the International Searching Authority for PCT/US06/048921, 5 pages (mailed Oct. 22, 2008).

*Primary Examiner* — Ryan Severson
(74) *Attorney, Agent, or Firm* — Jones Day; Nicola A. Pisano; Christopher C. Bolten

(57) ABSTRACT

Interventional catheters are disclosed for use in performing diagnostic and therapeutic procedures in vessels that are accessed retrograde to blood flow. The catheters include an elongated shaft slidably disposed within a sheath, a distal region having an end effector and a filter disposed proximal to the end effector to capture emboli liberated during the diagnostic or therapeutic procedure. The filter includes a plurality of struts that cooperate with an exterior surface of the catheter to define a reservoir to retain captured emboli, the reservoir configured so that advancement of the sheath contracts the filter without squeezing or dislodging captured emboli beyond a distal end of the filter.

20 Claims, 4 Drawing Sheets

INTERVENTIONAL CATHETER FOR RETROGRADE USE HAVING EMBOLIC PROTECTION CAPABILITY AND METHODS OF USE

CROSS-REFERENCE TO RELATED APPLICATIONS

This application is a continuation of U.S. patent application Ser. No. 11/315,463, filed Dec. 21, 2005, now U.S. Pat. No. 7,837,702, the entire contents of which are incorporated herein by reference.

FIELD OF THE INVENTION

The present invention relates generally to catheters for performing interventional procedures, such as angioplasty and/or stenting, in vessels where there is a risk of the release of one or more emboli. In particular, the present invention is designed for use in instances where the target vessel is accessed distal to the lesion or in the so-called "retrograde" fashion as in the iliac arteries when approached via ipsilateral femoral access.

BACKGROUND OF THE INVENTION

Interventional techniques have been developed wherein catheters are used to perform diagnostic and therapeutic procedures, such as stenting and angioplasty. During such procedures, thrombus, plaque, or other material may be released into the bloodstream as emboli. If free to circulate through the body, emboli may become lodged in the smaller distal vessels often with serious consequences, thereby presenting a risk of life-threatening or limb threatening ischemia.

U.S. Pat. No. 5,011,488 to Ginsburg, for example, describes a catheter designed to remove frangible thrombus from a vessel, such as from a A-V fistula, to restore flow through the vessel and reduce the risk that thrombus may dislodge and migrate to other regions of the patient's vasculature. The catheter comprises three concentrically arranged flexible tubes, wherein the innermost tube has at its distal end an expandable body and the central tube has an expandable funnel-shaped member. In operation, the funnel-shaped member is deployed proximal of the thrombus while the innermost tube and expandable member are advanced to a position distal of the thrombus. The expandable member then is deployed to contact the vessel wall and retracted proximally to urge the thrombus into the funnel-shaped member. U.S. Pat. No. 5,102,415 to Guenther et al. describes another multi-catheter device for use in removing blood clots.

The devices described in the foregoing patents have several disadvantages that limit their utility. First, the presence of multiple concentric catheters increases the delivery profile and rigidity of the device. Second, the devices are configured primarily to remove frangible thrombus, and are expected to be unsuitable for removing calcified or dense lesions without inflicting trauma to the vessel endothelium. Third, the configuration of the funnel-shaped components and retractable innermost catheter are incompatible with dilatation or stent delivery functionality.

U.S. Pat. No. 5,549,626 to Miller et al. describes a vena cava filter including a self-expanding mesh basket affixed to the distal end of an inner catheter enclosed within a delivery sheath. Suction may be applied through the inner catheter to remove emboli captured in the basket. As in the Ginsburg and Guenther patents, the device described in Miller is not appropriate for use in connection with stent delivery or vessel dilatation.

U.S. Pat. No. 4,723,549 to Wholey describes a catheter having an expandable filter mounted to the catheter shaft distal to a dilatation balloon. The filter comprises a plurality of ribs that are preformed to stow against the catheter. A balloon located between the ribs and catheter causes the ribs to deploy radially outward when inflated. The ribs and filter return to the collapsed position when the balloon is deflated.

The device described in the foregoing Wholey patent contemplates antegrade blood flow, i.e., in a proximal to distal direction along the catheter shaft. Accordingly, the device described in the Wholey patent would not be suitable for capturing emboli in the retrograde access applications, such as in the iliac arteries. In addition, there is a risk that, when the balloon deflates and the ribs collapse against the catheter shaft, some of the emboli collected in the filter may be squeezed past the end of the filter and escape into the bloodstream.

U.S. Pat. No. 6,042,598 to Tsugita et al. describes a variety of percutaneous catheter-based embolic filters. That patent discloses a number of filters that may be deployed from a distal end of a catheter. Like the filter in the aforementioned Wholey patent, however, such filters are not suitable for retrograde access applications, because the emboli are generally released downstream of the filters. In addition, FIG. 10 of Tsugita et al. depicts a catheter for use in retrograde access applications in which the filter assembly is coupled directly to the outer surface of the catheter. Such an arrangement is undesirable because it permits movements of the catheter to be directly transferred to the filter, thus creating the risk that emboli may escape past the outer edge of the filter. More importantly, however, the filter described with respect to FIG. 10 does not provide any mechanism for preventing large amounts of embolic material from being squeezed out of the filter by the sheath during filter contraction and removal of the catheter.

U.S. Patent Application Publication No. US2002/0095172 to Mazzocchi et al. describes various embolic filters that attempt to prevent emboli from escaping filters when they are contracted for removal. The filter of FIGS. 13-15 comprises a basket having a cover slidably disposed to engage the basket and thereby retain emboli within the filter. However, the relative complexity of the filters described in that application would appear to limit the utility of those designs.

In view of the foregoing, it would be desirable to provide a catheter for use in an interventional procedure in retrograde access applications, such as the iliac vessels, wherein the catheter has an embolic protection capability and provides a reduced insertion profile.

In view of the foregoing, it would be desirable to provide a catheter for use in an interventional procedure in retrograde access applications, such as the iliac vessels, wherein the catheter has an embolic protection capability and a simple design that avoids the use of multiple concentric catheters.

It further would be desirable to provide a catheter for use in an interventional procedure in retrograde access applications, wherein the catheter has an embolic protection capability and does not require suction or aspiration, thereby obviating the need to provide a suction or aspiration lumen and enabling a smaller insertion profile.

It also would be desirable to provide a catheter for use in an interventional procedure in retrograde access applications, wherein the catheter has an embolic protection capability and reduces the risk that emboli will be dislodged from the device during filter contraction and removal of the catheter.

SUMMARY OF THE INVENTION

In view of the foregoing, it is an object of the present invention to provide a catheter for use in an interventional procedure that requires retrograde access, such as the iliac vessels, wherein the catheter has an embolic protection capability and provides a reduced insertion profile.

It is another object of the present invention to provide a catheter for use in an interventional procedure in retrograde access applications, such as the iliac vessels, wherein the catheter has an embolic protection capability and a simple design that avoids the use of multiple concentric catheters.

It is also an object of this invention to provide a catheter for use in an interventional procedure in retrograde access applications, wherein the catheter has an embolic protection capability and does not require suction or aspiration, thereby obviating the need to provide a suction or aspiration lumen and enabling a smaller insertion profile.

It is a further object of the present invention to provide a catheter for use in an interventional procedure in retrograde access applications, wherein the catheter has an embolic protection capability and reduces the risk that emboli will be dislodged from the device during contraction and removal of the catheter.

These and other objects of the present invention are accomplished by providing an interventional catheter for use in retrograde access applications, such as the iliac arteries, having a filter that captures and securely retains emboli within a reservoir when the filter is collapsed for removal from the vessel. In a preferred embodiment, the catheter comprises a catheter having a therapeutic or diagnostic end effector, e.g., a balloon for dilatation or stent delivery, a filter disposed on the catheter shaft proximal of the end effector and a reservoir disposed between the filter and the end effector. The device preferably further comprises a delivery sheath that surrounds the catheter and assists in retracting the filter to its delivery configuration.

When used to treat stenotic lesions occurring in an artery that requires retrograde access, such as an iliac artery being treated from the ipsilateral femoral artery, the catheter is advanced through the artery until the end effector is disposed within the lesion, as may be determined by radiography. The sheath then is withdrawn proximally beyond the end effector and filter, allowing the filter to deploy. The end effector then is actuated to perform a desired diagnostic or therapeutic function, e.g., a balloon is inflated to dilate the lesion and/or deploy a stent and restore patency to the vessel.

In accordance with the principles of the present invention, emboli released during actuation of the end effector are captured in the filter and directed into the reservoir. Upon completion of the interventional procedure, the sheath and inner catheter are moved relative to one another to collapse the filter, thereby sealing the emboli within the reservoir and reducing the risk of an inadvertent release of particles. The catheter then is removed from the patient.

In one embodiment, the reservoir constitutes a reduced diameter section of the catheter shaft. In this embodiment, when the filter is contracted against the catheter shaft by advancement of the sheath, the filter spans the reduced diameter section of the shaft and imparts no squeezing motion to the captured embolic material. Accordingly, the captured embolic material cannot be squeezed past the distal end of the filter and is securely retained in the reservoir.

In an alternative embodiment, filter mesh has an amphora shape wherein the distal ends of the struts that support the filter mesh include a concave indentation, so that the proximal portion of the filter defines a reservoir. The indentation is configured so that when the sheath is advanced to contract the struts, the distal ends of the filter contact the catheter shaft before more proximal portions of the struts, and prevent embolic material from being dislodged from the filter in a distal direction.

Methods of using devices constructed in accordance with the present invention also are provided.

BRIEF DESCRIPTION OF THE DRAWINGS

The above and other objects and advantages of the present invention will be apparent upon consideration of the following detailed description, taken in conjunction with the accompanying drawings, in which like referenced characters refer to like parts throughout, and in which.

DETAILED DESCRIPTION OF THE INVENTION

The present invention is directed to an interventional catheter for use in the retrograde access applications, such as the iliac arteries, that includes an embolic protection system. In an iliac stenting procedure, for example, an interventional catheter is inserted percutaneously or through a cut-down in the patient's groin in the region of the femoral artery, whereby the blood flows towards the device along the catheter shaft, i.e., from the distal end of the device towards its proximal end. A catheter that incorporates a filter element located distal to the dilatation or stent delivery balloon, such as the above-described U.S. Pat. No. 4,723,549 to Wholey, cannot practically be used in such a procedure, since any emboli liberated will be carried away from the filter.

Figure 1A:
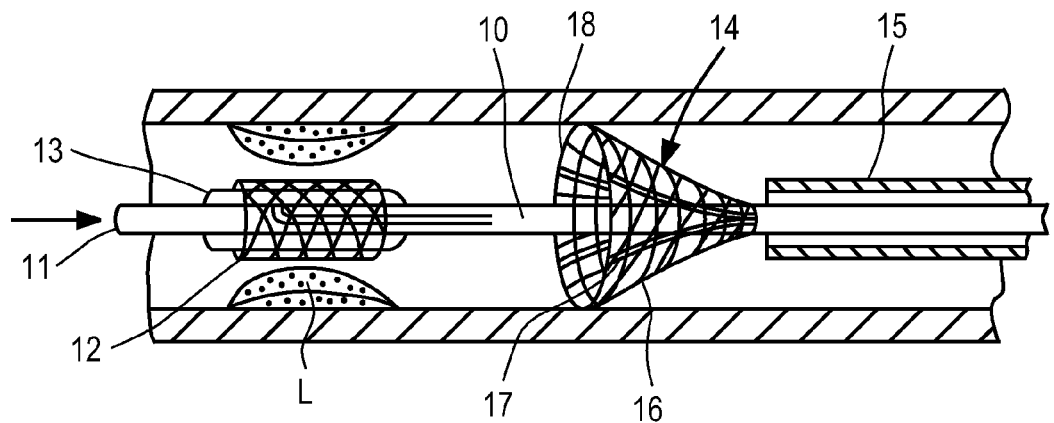
FIGS. 1A and 1B are side views of a prior art catheter for use in retrograde access applications depicting some of the shortcomings of such designs.

Referring to FIG. 1A, the stent delivery system and filter arrangement depicted in FIG. 10 of the foregoing U.S. Pat. No. 6,042,598 to Tsugita et al. is reproduced. Stent delivery system 10 comprises catheter 11 having stent 12 disposed on balloon 13, filter 14 and sheath 15 slidably disposed on catheter 11. Filter 14 comprises filter mesh 16 affixed to self-expanding struts 17. Sheath 15 retains struts 17 contracted against the shaft of catheter 11 during insertion of the catheter. Sheath 15 then is retracted proximally so that struts 15 self-expand and deploy filter mesh 16 to the funnel shape depicted in FIG. 1A. To ensure that emboli do not escape past the outer edge of filter 14, open end 18 of the filter contacts the vessel wall.

Stent delivery system 10 provides a filter suitable for use in retrograde access applications, i.e., where blood flows from the distal to the proximal catheter direction, as indicated by arrow A. Emboli E liberated during the stent delivery and dilatation procedure are captured in filter mesh 16. Upon completion of the interventional procedure, sheath 15 is advanced distally to collapse the filter and permit retrieval of the catheter. Alternatively the filter may have an atraumatic outer surface such that the catheter may be retracted into the sheath to close the filter.

Figure 1B:
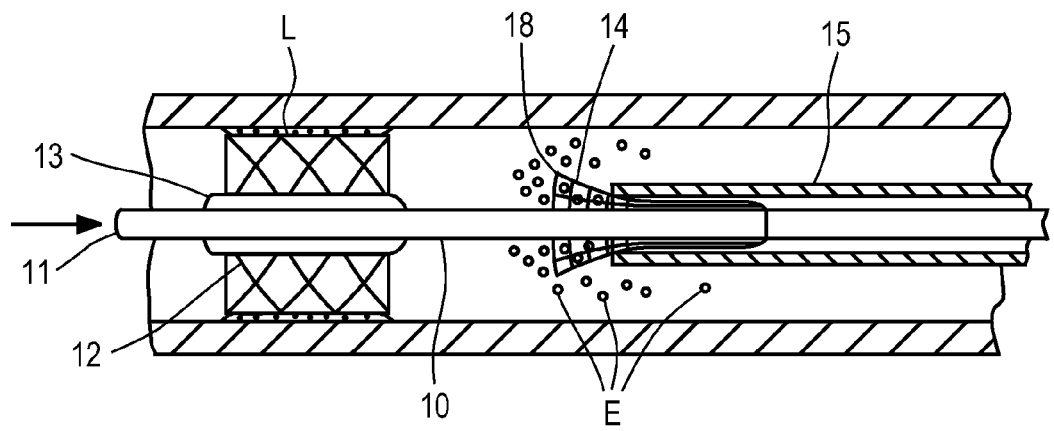

Referring to FIG. 1B, a principal drawback of the foregoing prior art catheter system is described. In particular, when sheath 15 is advanced forward, it causes struts 17 and filter mesh 16 to collapse against the shaft of catheter 11 in a proximal to distal direction. This is expected to squeeze captured embolic material distally towards open end 18 of filter 14, where it can escape from the filter into the bloodstream. The present invention is directed to solving this problem.

In accordance with the principles of the present invention, the interventional catheter of the present invention includes a filter configured to cooperate with a reservoir to ensure that embolic material captured by the filter is not inadvertently released when the filter is contracted for removal. More preferably, the device of the present invention includes a filter that seals the reservoir to prevent embolic material from escaping the filter during contraction and removal of the filter from the patient's vessel.

Figure 2:
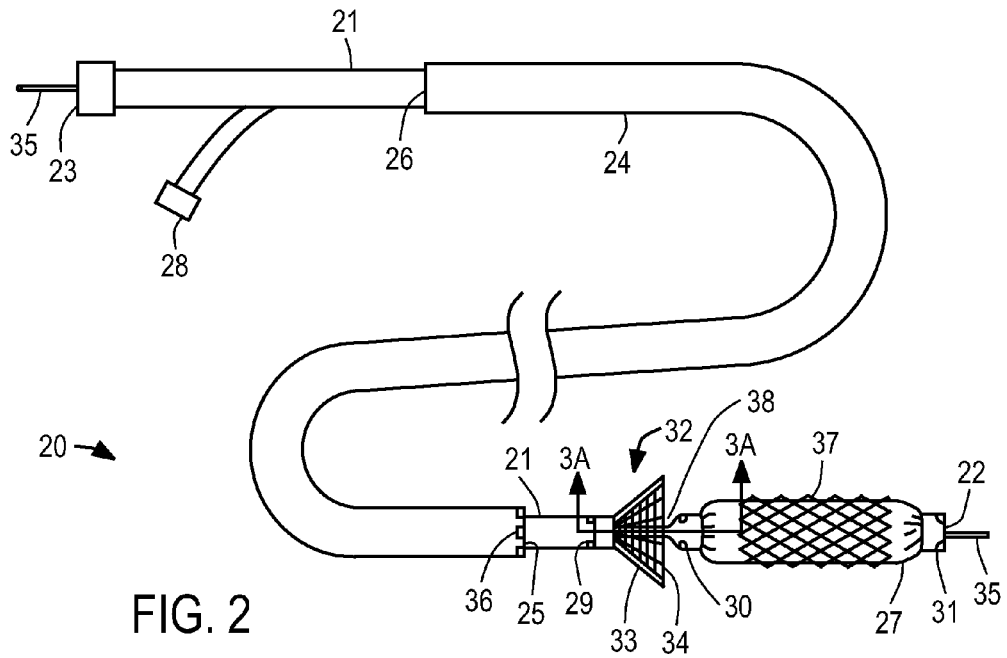
FIG. 2 is a side view of an exemplary embodiment of an interventional catheter of the present invention.

Referring now to FIG. 2, exemplary catheter 20 constructed in accordance with the principles of the present invention is described. Illustratively, catheter 20 comprises a stent delivery system, although it should be understood that the system could alternatively comprise a dilatation system, atherectomy system or other interventional diagnostic or therapeutic system.

Catheter 20 comprises catheter shaft 21 having distal end 22 and proximal end 23. Shaft 21 is slidably disposed within sheath 24 having distal end 25 and proximal end 26. Catheter 20 further comprises a distal region carrying a diagnostic or therapeutic end effector, illustratively balloon 27, inflation port 28 in communication with interior of the balloon, optional radiopaque markers 29, 30 and 31, and filter 32. Filter 32 comprises plurality of self-expanding struts 33 that support filter mesh 34, as described herein below.

Catheter 20 further comprises a guide wire lumen through which guide wire 35 may be slidably disposed. For over-the-wire use, the guidewire lumen extends from the distal end 22 to a port at proximal end 23 of catheter 20. Alternatively, rapid-exchange functionality, the guide wire lumen may extend from distal end 22 to a port comprising a lateral skive in the exterior surface of catheter shaft 21 about 8-10 centimeters proximal of filter 32. In either case, the guidewire lumen extends through the distal region of catheter shaft 21 including filter 32 and the end effector.

Sheath 24 optionally may include radiopaque marker 36 disposed at distal end 25 to permit fluoroscopic confirmation of the location of the sheath. Illustratively, balloon 27 has plastically deformable stent 37 disposed on its exterior surface, although any suitable stent and delivery mechanism may be employed with the embolic protection system of the present invention.

Catheter shaft 21 and sheath 24 preferably are formed of flexible biocompatible materials, such as polyethylene, polyurethane, PEBAX, nylon and other polymers typically used in catheter construction. Catheter shaft 21 optionally may comprise carbon nanotubes or other additives for added strength. Sheath 24 likewise may be formed in a conventional manner from known catheter materials. Balloon 27 preferably comprises a non-compliant or semi-compliant material, such as polyethylene or nylon, and may be constructed using balloon molding techniques that are per se known.

Figure 3A:
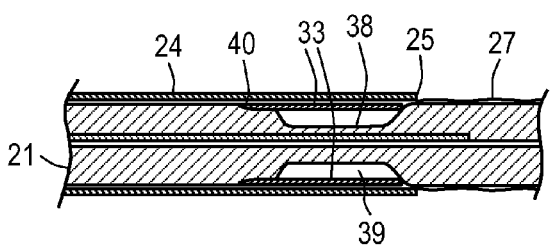
FIGS. 3A and 3B are side sectional views of the device depicted in FIG. 2 taken along the line A-A when in a contracted and a deployed state, respectively.
Figure 3B:
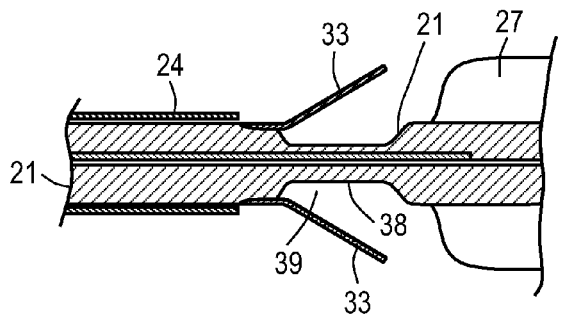

Referring now also to FIGS. 3A and 3B, which omits filter mesh 34 for clarity, catheter shaft 21 includes reduced diameter section 38 disposed adjacent to filter 32. Reduced diameter section 38 is shorter than the length of struts 33, so that when the struts are contracted against catheter shaft 21, filter 32 and reduced diameter section 38 cooperate to form reservoir 39. Accordingly, as depicted in FIG. 3A, when struts 33 are contracted against the catheter shaft, the struts span the length of reduced diameter section 3, and together with filter mesh 34, positively seal reservoir 39. This in turn prevents the escape of embolic material captured within the reservoir.

In addition, because struts 33 are not expected to deflect appreciably into reduced diameter section 38 during distal advancement of sheath 24, advancement of the sheath will not squeeze or dislodge captured embolic material towards the open end of the filter. Consequently, the risk that emboli will be released from the filter into the blood flow during contraction and removal of the catheter is greatly reduced relative to previously-known catheter designs, such as depicted in FIG. 1.

In a preferred embodiment, sheath 24 has an inner diameter of 6.5 French and catheter shaft 21 has an outer diameter of approximately 5 French, narrowing to a diameter of about 3 French at reduced diameter section 40. Catheter 20 preferably has a length appropriate for over-the-wire or rapid exchange use, as may be desired for a particular application.

Filter mesh 34 preferably comprises a mesh having a pore size selected to allow the passage of blood, but not emboli, through the filter. Illustratively, filter mesh has a pore size less than 500 micrometers, and more preferably, 200 micrometers or less. Filter mesh 34 may be attached to struts 32 using a suitable adhesive, bonding, sonic welding, or other method known in the art.

Referring now also to FIGS. 3 and 4, struts 33 are coupled to mounting ring 40, which is affixed to catheter shaft 21 proximal of reduced diameter section 38. Struts 33 are provided in sufficient number so that the outer edge of the filter assumes a substantially circular shape that contacts the entire interior circumference of a target vessel when deployed. Preferably, the filter mesh is supported by at least four struts, and more preferably, six, eight or more struts.

Figure 4A:
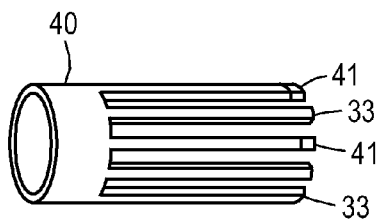
FIGS. 4A and 4B are side views of an embodiment of a self-expanding member in closed and open states, respectively.
Figure 4B:
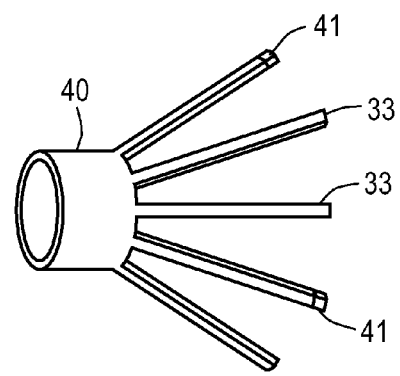

Struts 33 may comprise wire elements that are bonded to mounting ring 40. Alternatively, as depicted in FIGS. 4A and 4B, struts 33 and mounting ring 40 are integrally formed from a tube or flat sheet of metal, e.g., by laser cutting or etching. Struts 33 and mounting ring 40 preferably comprise a resilient metal alloy, and more preferably, a superelastic shape memory alloy, such as a nickel-titanium alloy. Although struts 33 are depicted as having a generally rectangular shape, it should be appreciated that the size, shape, geometry, and number of struts 33 may be varied to suit different applications.

As depicted in FIGS. 3A and 3B, catheter shaft 21, including reduced diameter section 38, may be integrally molded or machined from a tube of suitable biocompatible polymer. Alternatively, reduced diameter section 38 may comprise a short length of metal alloy hypotube, such as stainless steel, which is bonded at its proximal and distal ends to catheter shaft 21. This alternative construction advantageously may provide additional strength to the catheter in the vicinity of the reduced diameter section, and enhance pushability of the distal end of the catheter, especially with respect to a lesion comprising dense plaque.

Struts 33 preferably self-expand from the closed position depicted in FIG. 4A to the open position depicted in FIG. 4B upon proximal retraction of sheath 24. Struts 33 alternatively may comprise a shape memory alloy that is thermally actuated to transition between the open and closed position. For example, struts 33 may comprise a nickel-titanium alloy in which the expanded shape depicted in FIG. 4B has been impressed at high temperature. After placement of catheter 20 and retraction of sheath 24, a bolus of warm water may be injected around catheter 20, e.g., through the introducer catheter, to heat the struts to transition struts 33 and filter 32 to the deployed position. As a further alternative, mounting ring 40 and struts 33 may be resistively heated to transition the struts to the deployed position. In any of the foregoing embodiments, struts 33 are returned to the contracted position for removal by advancing sheath 24 to contact and collapse the struts against catheter shaft 21.

Still referring to FIGS. 4A and 4B, struts 33 may include radiopaque markers 41, visible under a fluoroscope, to confirm deployment of the filter 32. Markers 41 when deployed will have a substantially larger circumference than markers 29, 30, and 31 on catheter shaft 21 and marker 36 on sheath 24, thereby to facilitate rapid differentiation between filter 32, sheath 24 and catheter shaft 21.

Referring now to FIGS. 5A-5F, a method of using catheter 20 of FIG. 2 is described to protect against embolism during iliac stenting. With respect to FIG. 5A, the patient is prepped and the femoral artery is accessed percutaneously or via cutdown and an introducer (not shown) is placed to establish access to the patient's vessel V. Guidewire 35 is placed across lesion L and catheter 20 then is advanced along the guidewire until the stent is disposed across lesion L, as determined by fluoroscopic visualization of markers 30 and 31. Blood flow F is towards the operator, i.e., from the distal-to-proximal direction relative to device 10.

Figure 5A:
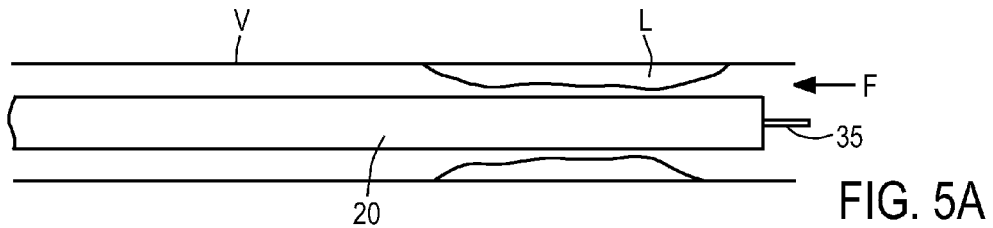
FIGS. 5A to 5F are side views illustrating steps of using the device of FIG. 2.
Figure 5B:
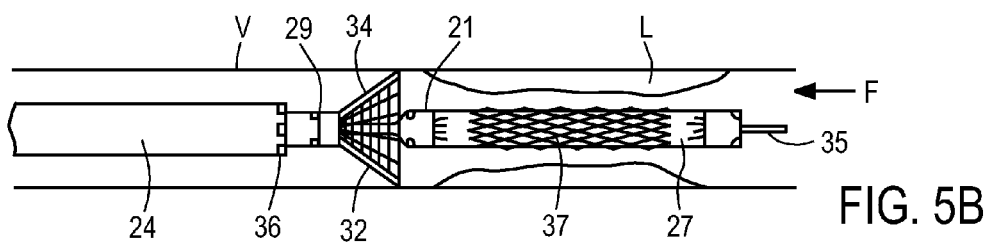

Once the position of catheter 20 is confirmed, sheath 24 is retracted proximally while holding catheter shaft 21 stationary. As depicted in FIG. 5B, sheath 24 is retracted to expose balloon 27, stent 37 and filter 32. As the sheath is retracted proximal to filter 32, struts 33 cause the filter to deploy so that filter mesh 34 spans the vessel. Proper retraction of sheath may be confirmed by using a fluoroscope to determine the relative positions of markers 29 and 27.

Figure 5C:
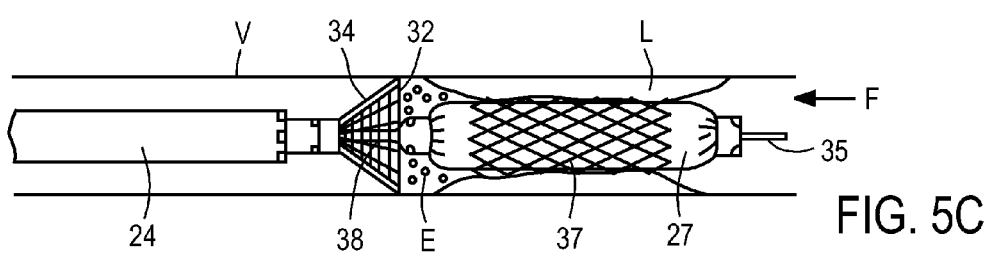

Balloon 27 then may be inflated by infusing contrast, saline or carbon dioxide through the inflation port and into balloon 27. As balloon 27 inflates, stent 37 is expanded into contact with lesion L, compressing the lesion against the vessel wall and restoring patency to the vessel. During stent deployment, pieces of plaque are released from lesion L, forming emboli E. Emboli E are carried downstream by blood flow F and are captured by filter 32 and are deposited in reservoir 38, as depicted in FIG. 5C.

Figure 5D:
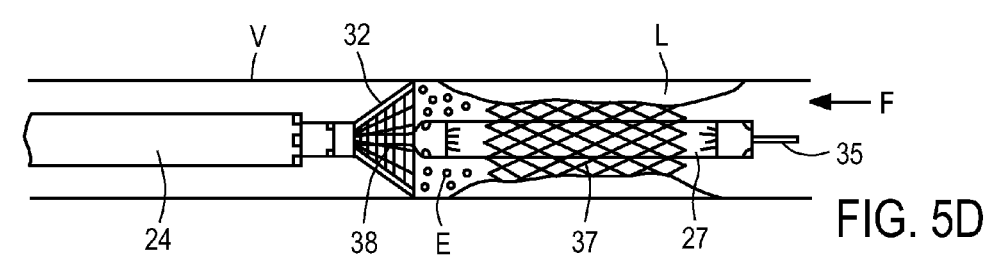
Figure 5E:
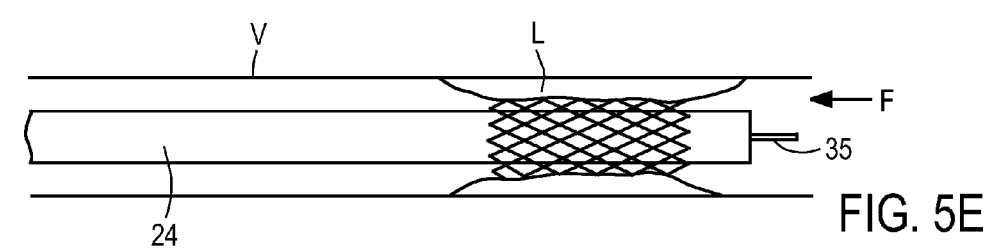

Referring now to FIG. 5D, after deployment of stent 37, balloon 27 is deflated. This process may release addition emboli E that are captured in filter 32. Sheath 24 is then advanced distally to cause struts 33 and filter mesh 34 to collapse and seal reservoir 38. As depicted in FIG. 5E, as sheath 24 is further advanced in the distal direction to cover balloon or the balloon is retracted, emboli are retained within the reservoir and cannot escape into the blood flow.

Figure 5F:
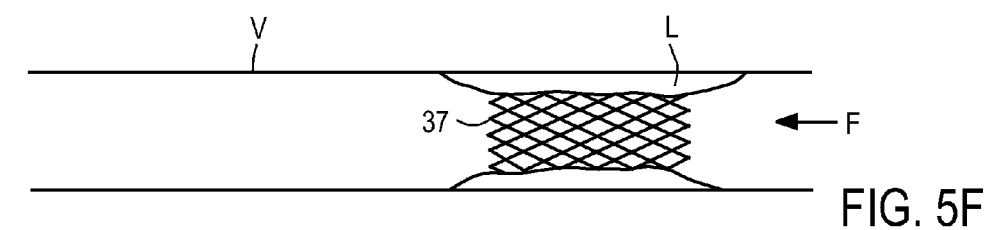

Referring to FIG. 5F, once sheath 24 has been advanced over filter 32 and/or balloon 27, catheter 20 may be removed, followed by removal of guide wire 35. Once catheter 20 is removed from the patient, emboli E collected in reservoir 38 may be examined. It should be appreciated that the foregoing method may be employed without stent 37 present on catheter 20, in case a simple dilatation procedure is desired.

Figure 6A:
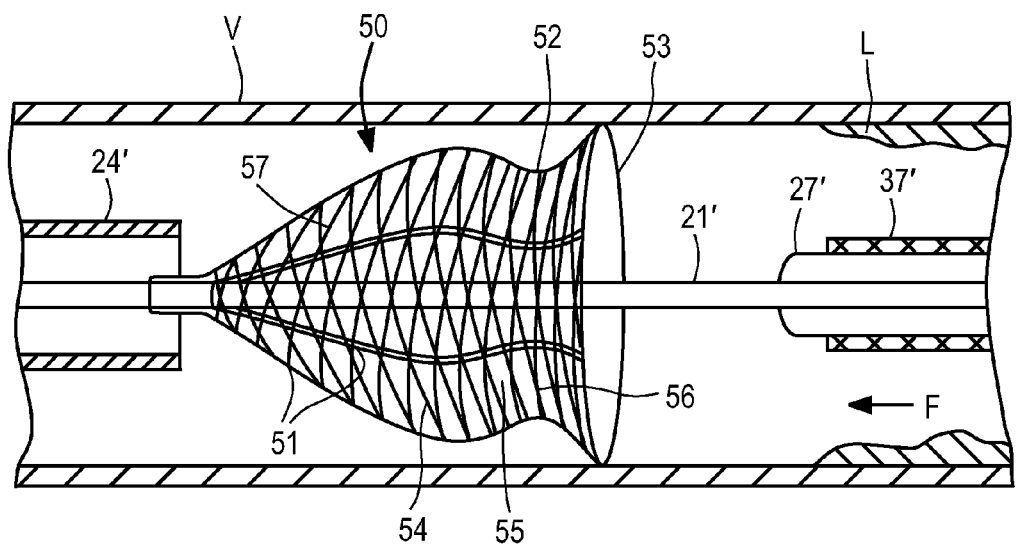
FIGS. 6A and 6B are side sectional views of an alternative embodiment of a filter suitable for use in the catheter of the present invention, deployed within a vessel and in a contracted state, respectively.
Figure 6B:
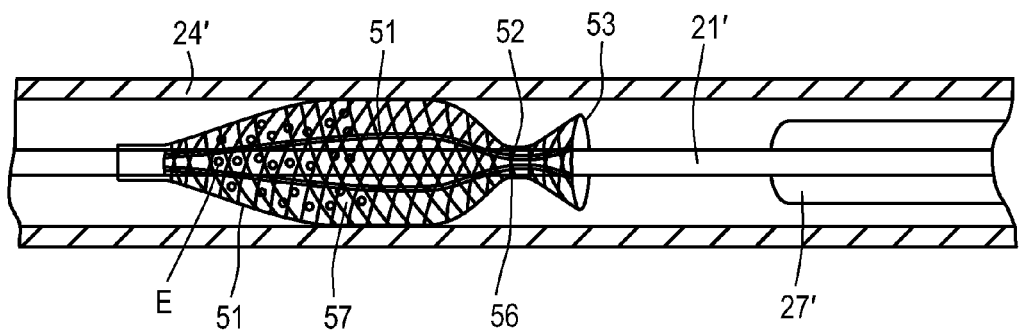

Referring now to FIGS. 6A and 6B, an alternative embodiment of a filter suitable for use in the catheter of the present invention is described. In particular, filter 50 may be directly substituted for filter 32 in catheter 20 of FIG. 2. In the following description, except where specifically noted, primed reference numbers refer to the corresponding structure of the embodiment of FIG. 2. Thus, for example, catheter 20' of FIG. 6A is shown disposed in vessel V and includes catheter shaft 21' slidably disposed within sheath 24'. Balloon 27' carries stent 37' for deployment within lesion L.

Filter 50 comprises plurality of struts 51 coupled at their proximal ends to catheter shaft 21'. The distal ends of each of struts 51 includes a concave indentation 52 which slopes outward to define opening 53 of the filter. Struts 51 are covered with filter mesh 54, for example, ePTFE having a multiplicity of pores 55, sized as described hereinabove. As depicted in FIG. 6A, concave indentations 52 form neck 56 that give the filter an amphora shape in the deployed position. In accordance with the principles of the present invention, the portion of filter 50 proximal of neck 56 defines reservoir 57 that retains emboli E captured by filter 50 during deployment of stent 37'.

Struts 51 operate in a manner similar to that described above for filter 32. In particular, struts 51 are held in a contracted delivery position by sheath 24', and self-expand radially outward to the amphora shape illustrated in FIG. 6A when sheath 24' is retracted proximally. Preferably, struts 51 comprise a shape memory alloy that has been trained, using known techniques, to retain concave indentations 52. The sloping surface of opening 53 is shaped so that embolic material liberated by actuation of the end effector, illustratively deployment of stent 37' by balloon 27', are funneled past neck 56 into the proximal portion of the filter.

Struts 51 are configured to collapse towards the exterior surface of catheter shaft 21' when sheath 24' is advanced distally upon completion of actuation of the end effector to return filter 50 to its delivery position. In accordance with one aspect of the present invention, concave indentations 52 of struts 51 contact the exterior surface of the catheter shaft 21' before the portion of the filter proximal to neck 56. In this manner, as sheath 24' is advanced distally, the struts seal reservoir 57, thereby preventing embolic material captured within the reservoir from being expelled past neck 56 of the filter. Accordingly, further advancement of sheath 24' over filter 50 cannot squeeze embolic material from the filter, reducing the risk of embolization during contraction and removal of the catheter.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. An interventional catheter for use in a vessel, comprising:
    an elongated shaft having an exterior surface, a proximal end, and a distal end; and
    an amphora-shaped filter coupled to the exterior surface of the elongated shaft, the filter comprising a plurality of expanding struts supporting a filter mesh, the struts configured to transition between a contracted position, wherein a concave portion of the struts contacts the exterior surface of the elongated shaft, and an expanded position, wherein the filter mesh is deployed to capture emboli, the filter defining a reservoir between the concave portions and a proximal portion of the struts when the plurality of struts is in the contracted position.

2. The catheter of claim 1 further comprising a sheath having a distal end slidably disposed on the elongated shaft, the sheath movable from a retracted position, wherein the distal end of the sheath is located proximal of the filter, to an extended position, wherein the distal end of the sheath collapses the filter such that the concave portions contact the exterior surface of the elongated shaft to seal the reservoir.

3. The catheter of claim 2 wherein the struts self-expand upon retraction of the sheath.

4. The catheter of claim 1 wherein the elongated shaft further comprises a diagnostic or therapeutic end effector located distal of the filter.

5. The catheter of claim 4 wherein the end effector comprises a balloon.

6. The catheter of claim 5 further comprising a stent disposed on the balloon.

7. The catheter of claim 1 wherein the filter mesh has a multiplicity of pores, the size of the pores sufficient to permit blood to pass through the filter, but to capture embolic material.

8. The catheter of claim 7 wherein the pore size is smaller than 500 micrometers.

9. The catheter of claim 1 wherein the plurality of struts comprises four or more struts.

10. The catheter of claim 1 further comprising one or more radiopaque markers affixed to the elongated shaft.

11. The catheter of claim 1 further comprising one or more radiopaque markers affixed to the plurality of struts.

12. The catheter of claim 1 wherein the plurality of struts are integrally formed with a mounting ring that couples the plurality of struts to the exterior surface of the elongated shaft.

13. The catheter of claim 12 wherein the plurality of struts and mounting ring comprise a superelastic alloy.

14. The catheter of claim 1 wherein the elongated shaft has a diameter of 5 French.

15. The catheter of claim 1 wherein the elongated shaft further comprises a guide wire lumen extending through the distal end of the elongated shaft.

16. A method of capturing emboli in a vessel, comprising:
advancing an interventional catheter into a vessel having a lesion such that the catheter is positioned adjacent to the lesion, the interventional catheter having a sheath, an elongated shaft slidably disposed within the sheath, and an amphora-shaped filter coupled to the elongated shaft;
retracting the sheath to a position proximal to the filter such that a plurality of struts supporting a filter mesh on the filter expand to capture emboli from the lesion; and
moving the sheath to a position distal to the filter such that a concave portion of the struts contacts the elongated shaft to define a reservoir between the concave portions and a proximal portion of the struts.

17. The method of claim 16 wherein the interventional catheter further comprises a balloon located distal of the filter, wherein the advancing comprises advancing the interventional catheter into the vessel such that the balloon is disposed across the lesion.

18. The method of claim 17 further comprising inflating the balloon to compress the lesion and release emboli after the retracting and before the moving.

19. The method of claim 16 wherein the interventional catheter is advanced along a guidewire.

20. The method of claim 16 further comprising determining a position of the interventional catheter using fluoroscopic visualization of one or more radiopaque markers affixed to the interventional catheter.

* * * * *